(12) United States Patent
Forstner

(10) Patent No.: US 6,231,517 B1
(45) Date of Patent: May 15, 2001

(54) APPARATUS AND A METHOD FOR NON-INVASIVE MEASUREMENT OF THE ARTERIAL BLOOD PRESSURE

(75) Inventor: Klaus Forstner, Asperg/Wurttemberg (DE)

(73) Assignee: Microlife Corporation (TW)

( * ) Notice: Subject to any disclaimer, the term of this patent is extended or adjusted under 35 U.S.C. 154(b) by 0 days.

(21) Appl. No.: 09/317,123

(22) Filed: May 24, 1999

Related U.S. Application Data

(60) Provisional application No. 60/087,078, filed on May 28, 1998.

(51) Int. Cl.[7] .................................................. A61B 5/02
(52) U.S. Cl. .......................... 600/485; 600/492; 600/500; 600/495
(58) Field of Search .................... 600/485, 490, 600/492, 499, 500, 503

(56) References Cited

U.S. PATENT DOCUMENTS

| | | | |
|---|---|---|---|
| 2,753,863 | * 7/1956 | Bailey | 600/499 |
| 3,633,567 | * 1/1972 | Sarnoff | 600/499 |
| 3,659,592 | * 5/1972 | Natanski | 600/499 |
| 4,549,550 | * 10/1985 | Kami | 600/499 |
| 4,993,422 | * 2/1991 | Hon | 600/503 |
| 5,509,423 | * 4/1996 | Bryars | 600/503 |
| 5,680,867 | 10/1997 | Shimazu et al. | |
| 5,908,027 | * 6/1999 | Butterfield et al. | 600/503 |

FOREIGN PATENT DOCUMENTS

| | | |
|---|---|---|
| 1-265941 | 10/1989 | (JP) . |
| 5-137730 | 6/1993 | (JP) . |
| 7-275213 | 10/1995 | (JP) . |
| 95/00070 | 1/1995 | (WO) . |
| 97/12542 | 4/1997 | (WO) . |

* cited by examiner

Primary Examiner—Robert L. Nasser
(74) Attorney, Agent, or Firm—Shoemaker and Mattare, Ltd.

(57) ABSTRACT

An apparatus (21) which measures the arterial blood pressure at the human wrist (1) is provided with a cuff (22) having a shape adapted to be placed in a predetermined position around the wrist (1). The cuff (22) has one or two inflatable measuring bladders (23a, 23b). The bladders (23a, 23b) are arranged and have a size in such a way that each bladder (23a, 23b) covers only one of either the radial (2) and the ulnar (3) artery.

8 Claims, 5 Drawing Sheets

APPARATUS AND A METHOD FOR NON-INVASIVE MEASUREMENT OF THE ARTERIAL BLOOD PRESSURE

This application claims priority from U.S. provisional patent application Ser. No. 60/087,078, filed May 28, 1998.

The invention relates to an apparatus and a method for non-invasive measurement of the arterial blood pressure according to the preamble of the independent patent claims.

Oscillometric blood pressure measurement was clinically introduced at the beginning of the 1980s. Although primarily intended to meet clinical requirements, the technology was additionally adapted to home-use devices with progress in both digital processing and memory technology. These advantages allowed the construction of inexpensive and highly transportable blood pressure measuring systems, widely applied in home use.

The oscillometric technology was originally developed to be applied at the brachial artery. This specific artery is also the site of the clinical reference measurement, performed by physicians and nurses. The brachial artery is covered by the biceps and triceps brachial muscles and is compressed in a well-defined manner by the cuff's compression at the upper limb. Since the brachium is located at the heart's level, the application site sufficiently fulfils the need of measuring at the correct position.

In order to place brachial cuffs correctly, clothes such as suits shirts or coats must be removed. Additionally, the application of the cuff requires a positioning manoeuvre by using the other arm. This procedure proves difficult in some elderly people and in patients suffering from certain diseases (e.g. brain stroke symptoms, neuro-system diseases, traumatic lesions of the upper limbs).

These limitations of the brachial arm blood pressure measurement were the basic motivation for several manufacturers to adapt the oscillometric measurement to new applications sites. So, in the early 1990s the wrist was introduced as an additional measurement site.

The human wrist is the interconnection between the forearm, composed of the radius and the ulna, and the carpal bones. The arteries passing the wrist supply all anatomical structures of the hand. There are two major arteries: the radial artery and the ulnar artery. Anatomical details are given in FIG. 1.

Both arteries are compressed and gradually released during the course of the oscillometric measurement. Thus, both arteries independently produce pressure pulses, which are detected by the pneumatic pressure sensor within the measuring device.

Basically, the oscillometric technology refers to a certain pulse pattern, described as the pulse oscillogram. The shape of this pulse oscillogram is the basis for the determination of the measurement results, the systolic and diastolic arterial blood pressure. The individual anatomy of the application site leads to a certain change of the pulse oscillogram's shape. This is why the oscillometric blood pressure measurement results differ from each other.

Basically, the measurement at two different arteries, the radial and ulnar artery, results in the detection of two different pulse oscillograms. These oscillograms overlap each other. The shape of these pulse oscillograms are usually not identical. The pressure detection system receives the summary signal of both oscillograms.

The overlapping of the radial and the ulnar pulse oscillogram varies highly since the histological structure is interindividually different. Therefore the overlapped signal is not defined concerning the pulse oscillogram's rising and falling signal curves. Both arteries contribute to the degree of scattering in the state of the art technology.

Since two different arteries contribute to the pulse oscillogram's shape, the variation of the overlapped total signal is fairly high. The overlapped signal's variation greatly exceed the variation of the signal of one single vessel. This is one reason why the results of wrist-type oscillometric measurements are less reliable than those of brachial applications.

It is an object of the present invention to overcome the drawbacks of the prior art, especially to provide an apparatus and a method for non-invasive measurement of the arterial blood pressure which is applicable at the human wrist and which leads to reliable measurements.

According the invention, these objects are solved by an apparatus and a method with the features of the characterizing portion of the independent patent claims. The method presented refers to one artery and therefore is diminishing the amount of scattering.

The apparatus for non-invasive measurement of the arterial blood pressure consists substantially of a cuff having at least one inflatable measuring bladder. The cuff has a shape adapted to be placed in a predetermined position around the human wrist. This specific shape allows the cuff to be placed at a predefined position for each measurement.

The cuff has one measuring surface which is adapted to be applied over the ulnar artery of the wrist and a second measuring surface area adapted to be applied over the radial artery of the wrist. Due to the shape of the cuff which allows exact positioning, the first and second measuring surface areas will always lie over the ulnar artery (first measuring surface area) and over the radial artery (second measuring surface area). The measuring bladder is connected with a blood pressure monitor, which allows indication of the diastolic and systolic blood pressure using an oscillometric measuring method.

According to the present invention, each of the measuring bladders (one or two bladders) has an angular extension and is disposed within the cuff in such a way that it is arranged within only one of the first and the second measuring surface areas.

Due to this specific disposition of the bladders, the pulses of only one artery is taken into account for a specific cuff, such that there is no overlapping of the pulse signals. This includes the design that both arteries are contributing separately to the signals in their specific cuffs.

One or two measuring bladders may be provided. According to a first aspect of the invention, the cuff comprises one bladder which is arranged in such a way that it contacts the first measuring surface area, i.e. that it lies over the ulnar artery when the cuff is applied to the wrist.

In another aspect of the invention, the cuff comprises one bladder which is arranged in such a way that it contacts the second measuring surface area, i.e. that it takes into account the pulses provided by the radial artery of the wrist.

It is also conceivable to use a cuff which is provided with two bladders. In such an arrangement, a first bladder is arranged in such a way that it contacts only the first measuring surface area and a second bladder is arranged in such a way that it contacts only the second measuring surface area. With such an arrangement, it is important that the signals of the two bladders are treated separately in the blood pressure monitor. As the pulses of both arteries are treated separately, the stability of the measurement may be enhanced significantly. This is due to the fact that two blood pressure measurements are taken separately at the same time and consequently are used to minimise possible artefacts.

In a preferred embodiment, the cuff comprises at least one marking which allows positioning of the cuff around a wrist. The cuff already has a shape which is adapted to be placed in a predetermined position around the wrist. The marking facilitates positioning of the cuff for the user and ensures a correct application of the cuff.

In a further preferred embodiment, each bladder is provided with a pneumatic pressure tube which is connected by a connector to the blood pressure monitor. In the case of the two-bladder design, a pneumatic double tube is preferably used, each of the said bladders being connected with one of the tubes. This allows electronic signal processing of the two signals. The combined analysis of these two signals intends to enhance the artefact suppression as well as improve the measurement stability.

There may be basically three types of measuring apparatus according to the present invention. A first ulnar type has one bladder which is arranged in the first, ulnar, measuring surface area. A second radial type has a bladder which is arranged in the second, radial, measuring surface. A third so-called dual type comprises two bladders, a first bladder which is arranged in the first, ulnar, measuring surface area and a second bladder which is arranged in the second, radial, measuring surface area.

These types of cuffs may be used with one and the same blood pressure monitor. Preferably, the connector connecting the cuff with the blood pressure monitor is provided with a code representing the location of the cuff, i.e. a coding which shows whether the cuff is of the ulnar, the radial or the dual type. The coding is detectable by the blood pressure monitor which therefore is operated in an appropriate mode.

It is preferred that the bladder extends over certain angle ranges; these are approximately:

Ulnar cuff: ulnar: 40°–150°
Radial cuff: radial: 40°–150°

The precise design depends on the age and the wrist circumference of the individual patient group.

Such an angular extension of the cuff ensures that no bladder covers both the ulnar and radial artery, but that each of these arteries is sufficiently covered by their specific bladder.

The method according to the present invention uses a measurement which is based on a signal provided by only one of the ulnar and the radial artery. In another aspect of the invention, the method is based on two signals, one signal being provided by the ulnar artery and the other signal being provided by the radial artery. According to the invention, the two signals are separately treated in order to determine two measuring values. The blood pressure is calculated based on these two measuring values in a calculating unit. The combination of these two signals is used to reduce measurement stability and to increase the accuracy of the results.

Several cuff and/or bladder sizes may be provided, allowing correct measurements to be taken of a broad selection of patients, including small children and large circumference wrists. The cuff is labelled with the clinically approved specific range of the wrist circumference.

The invention lowers the artificial variation of the wrist-type technology. This is done by a separate detection of the arterial pulse signals. By this measure the interaction by the two independent vessels is eliminated. The determination of the systolic and diastolic pressure by the blood pressure computer is based on a stable pulse oscillogram, which is not adversely affected by the interaction of a second arterial vessel.

The invention is realised by a specific cuff design in combination with a certain non-invasive blood pressure monitor. This monitor is able to process either the ulnar artery pulses, the radial artery pulses or both measurement values in parallel. Such monitors are well known to those skilled in the art.

The invention will now be described in more detail with reference to the embodiments and the figures, in which.

Figure 1:
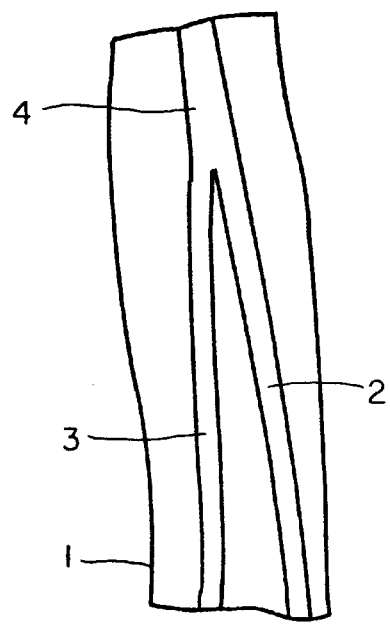
FIG. 1 is a schematic view of a human arm.

FIG. 1 schematically shows a human wrist 1. In the area above the wrist 1, the brachial artery 4 is divided in the radial artery 2 and in the ulnar artery 3. According to the present invention, blood pressure is measured with a cuff arranged in the area of the radial artery 2 and the ulnar artery 3.

Figure 2:
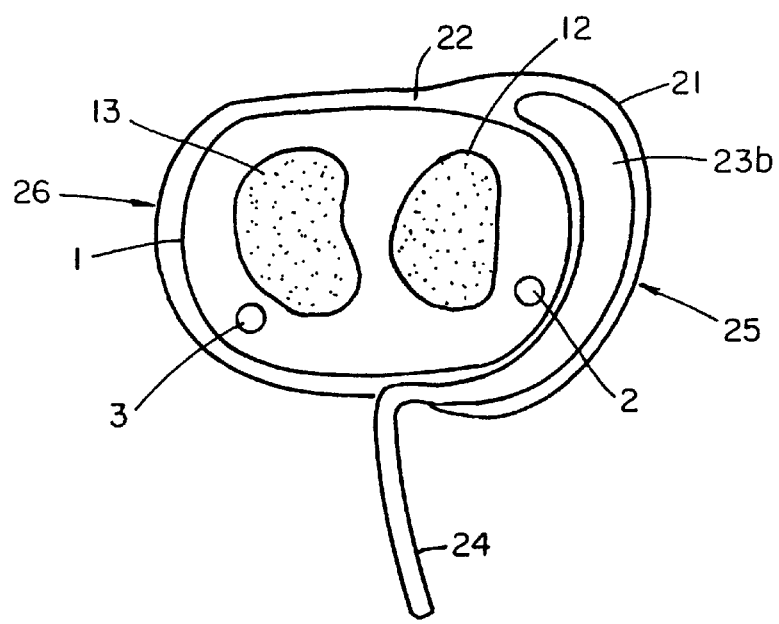
FIG. 2 is a cross-section through a human wrist with a first embodiment of the measuring device.

FIG. 2 shows a cross-section through the human wrist 1 with an apparatus 21 for measuring the blood pressure according to the present invention. The wrist 1 comprises two bones, the radius 12 and the ulna 13, and a radial artery 2 and an ulnar artery 3.

The apparatus 21 comprises a cuff 22 which is provided with an inflatable bladder 23b. The bladder 23b is connected to a blood pressure monitor (not shown) by a pressure tube 24.

The cuff comprises a first measuring surface area 25 and a second measuring surface area 26. According to the invention, the inflatable bladder 23b is arranged only within the first, radial, measuring surface area 25. The inflatable bladder 23b therefore covers the radial artery 2, but not the ulnar artery 3.

Figure 3:
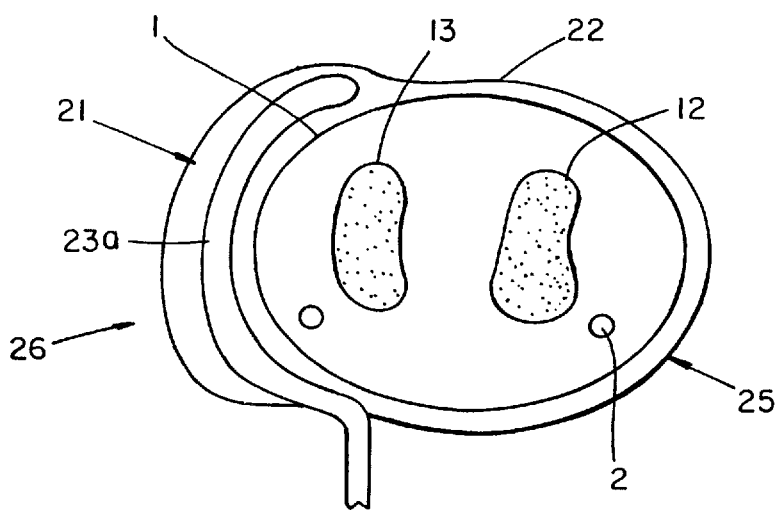
FIG. 3 is a cross-section through a human wrist with a second embodiment of the apparatus.

FIG. 3 shows an embodiment of the invention of the ulnar type. A cuff 22 is disposed on a human wrist 1. The cuff 22 comprises an inflatable bladder 23a, which is arranged in a second measuring surface area 26 of the cuff 22. The bladder 23a is arranged only in the second, ulnar, measuring surface area 26 and therefore covers the ulnar artery 3, but not the radial artery 2. A pressure tube 24 connects the bladder 23a with a blood pressure monitor (not shown).

Figure 4:
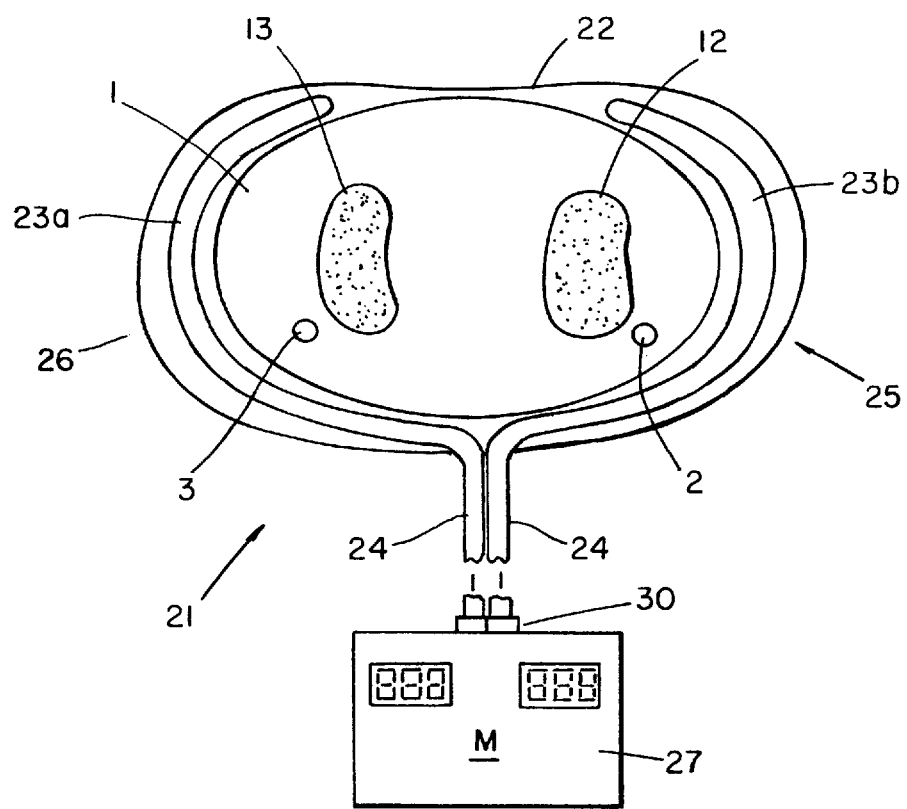
FIG. 4 is a cross-section through a human wrist with an apparatus according to the third embodiment of the invention.

FIG. 4 shows a dual embodiment of the present invention. As in FIGS. 2 and 3, a cuff 22 is placed around a human wrist 1. The cuff 22 comprises two inflatable bladders 23a, 23b. The first bladder 23b is arranged in a first, radial, measuring surface area 25 which covers the radial artery 2. The second bladder 23a is arranged in a second, ulnar, measuring surface area 26 and covers the ulnar artery 3. The two bladders 23a, 23b are separately connected to a blood pressure monitor 27 by two separate pressure tubes 24 of a pneumatic double tube. The tubes 24 are connected to the blood pressure monitor by a connector 30. The connector 30 is provided with a coding which allows the blood pressure monitor 27 to detect if the cuff is of the radial, the ulnar or the dual type.

The cuff 22, the pressure tubes 24 and the pressure monitor 27 from an apparatus 21 for non-invasive measurement of the arterial blood pressure at the human wrist according to the present invention.

Figure 5A:
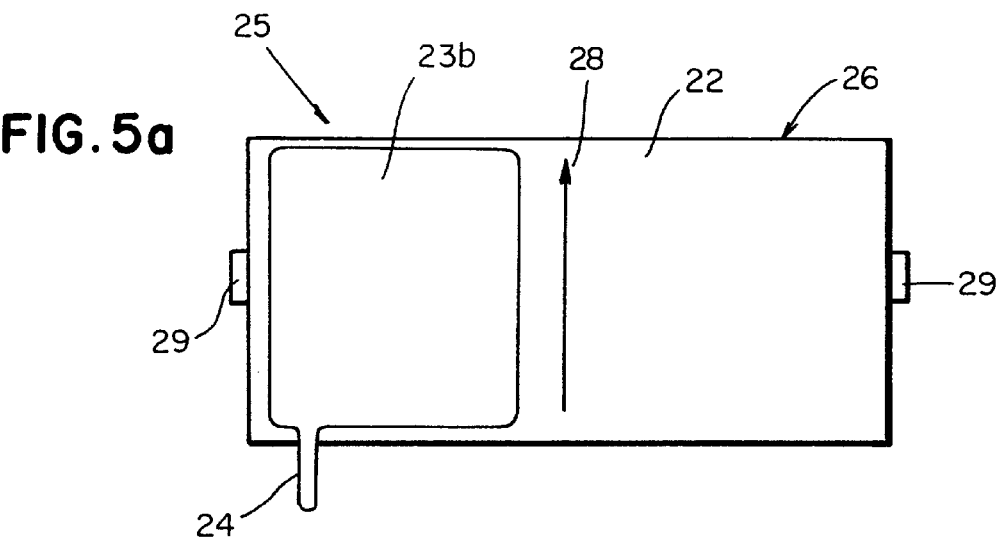
FIGS. 5a–5c are schematic representations of the cuffs of FIGS. 2–4.
Figure 5B:
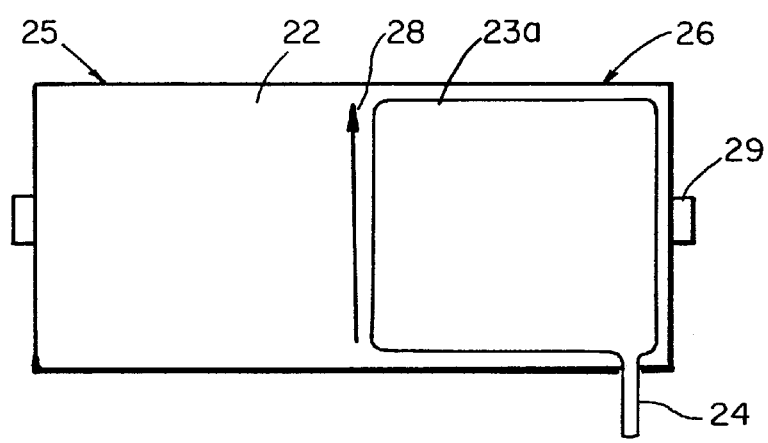
Figure 5C:
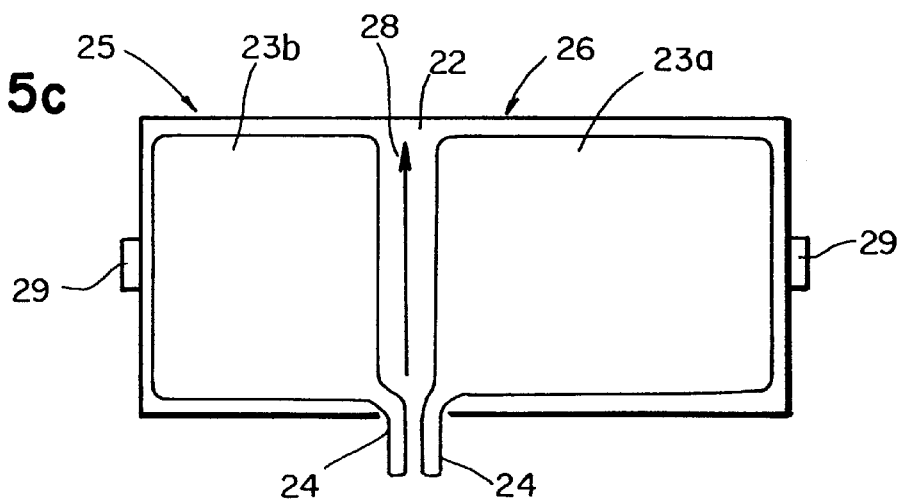

FIGS. 5a to 5c show different embodiments of the cuff 22 is a schematic way. FIG. 5a shows a cuff 22 of the ulnar type. An inflatable bladder 23b is disposed within the cuff 22 such that it will sufficiently contact the ulnar artery 3 of a wrist when it is applied to the wrist. The cuff 22 further comprises a marking 28 which facilitates positioning of the cuff 22 around the wrist. The cuff 22 further comprises locking means 29 which allow the cuff 22 to be applied tightly around the wrist. The bladder 23b, which is arranged in a first measuring surface area 25 (adapted to be placed over the ulnar artery 3 of the wrist), is connected with a pressure tube 24 to a blood pressure monitor (not shown).

FIG. 5b shows a cuff 22 of the radial type. The inflatable bladder 23a is arranged in a second measuring surface area 26, which is adapted to be placed over the radial artery 2 of a wrist.

FIG. 5c shows a cuff 22 of the dual type. The first and second inflatable bladders 23a, 23b are each provided with a pressure tube 24 and are separately connected to a blood pressure monitor.

Figure 6A:
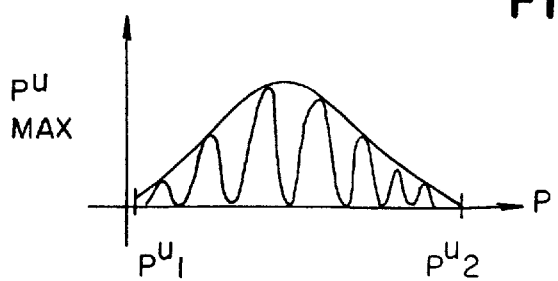
FIGS. 6a–6c are representations of a ulnar pulse oscillogram, a radial pulse oscillogram and summarised pulse oscillogram of prior art devices.
Figure 6B:
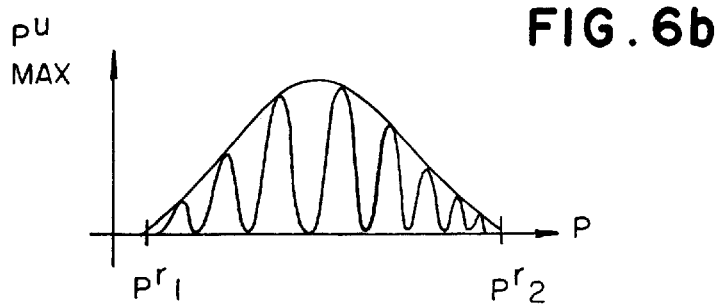

FIGS. 6a 6b show an oscillogram indicating the measuring values taken on the ulnar artery (FIG. 6a) and from the radial artery (FIG. 6b).

Figure 6C:
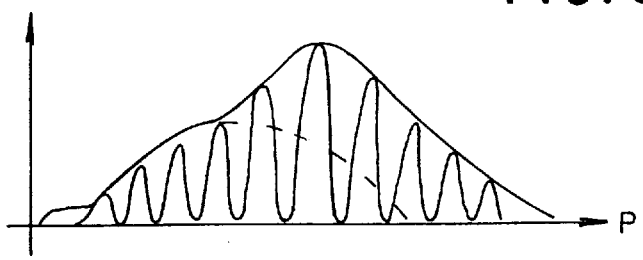
Figure 6D:
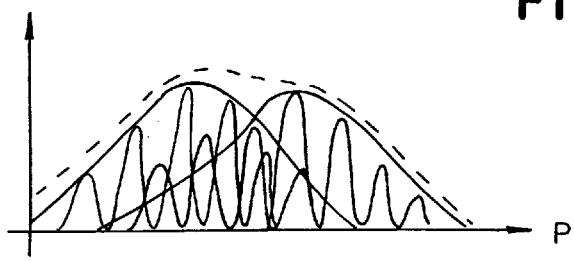

FIGS. 6c and 6d show an oscillogram taken with a measuring apparatus according to the prior art, wherein one bladder measures at the same time both the pressure in the ulnar and in the radial arteries. This combination of the two pulses leads to an undefined summarized pulse oscillogram.

The dual bladder versions intends to minimize the result's variation and to improve the measurement accuracy. This is done by comparing both pulse oscillograms. The pulse oscillogram with inherent erroneous signal sequences with be excluded. If both pulse oscillograms are valid, the measurement results will be combined, e.g. averaged.

Each bladder is characterised by a specific connector type. This connector 30 codes for the specific application site and different cuff sizes (specific age groups). The coding is performed by mechanical, electrical or electronic measures. For example, the coding is performed by the length of the male tube connector.

Figure 7:
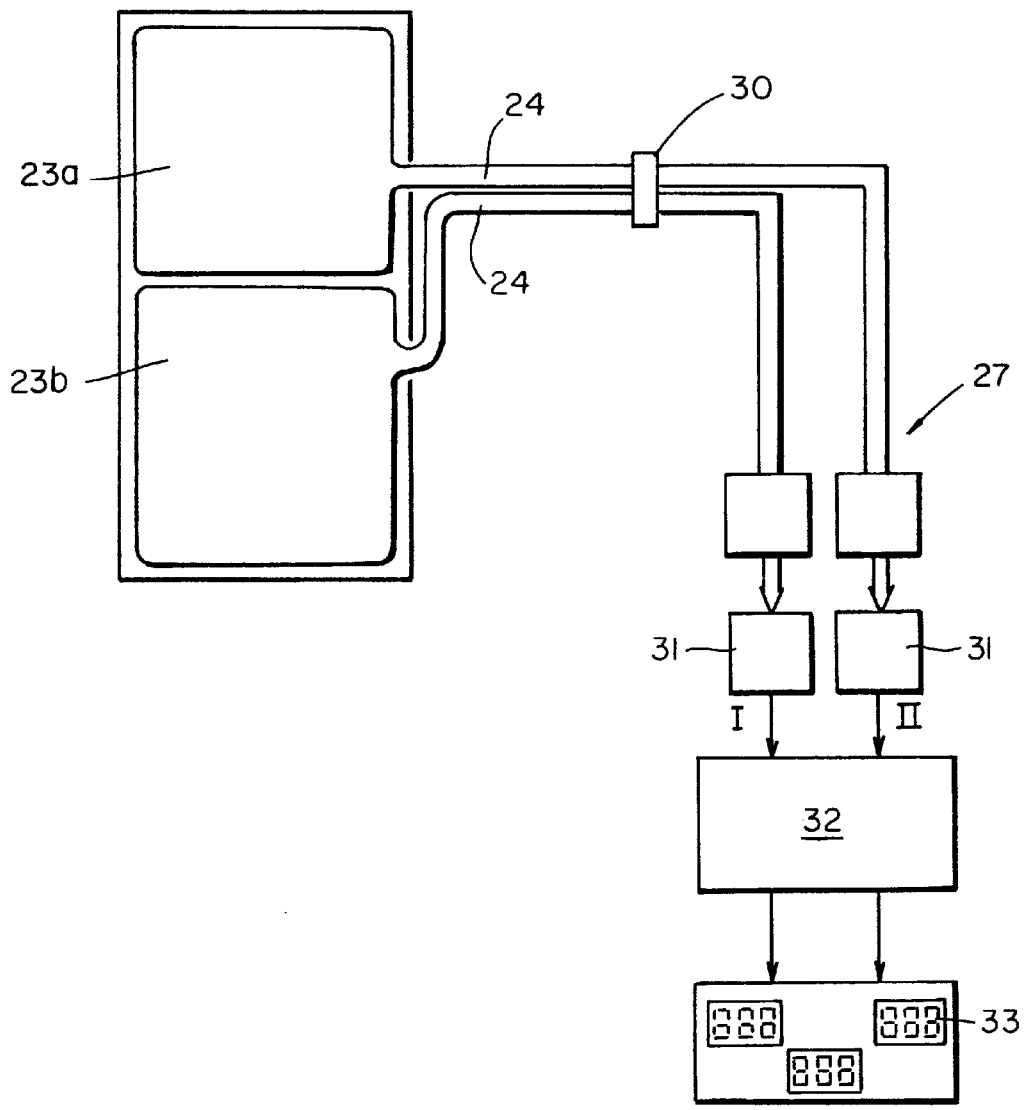
FIG. 7 is a schematic view of a dual type measuring device.

FIG. 7 schematically discloses a dual type embodiment of the cuff and a blood pressure monitor 27. Two bladders 23a, 23b are separately connected to the blood pressure monitor 27 by a connector 30. In the blood pressure monitor 27, the pressure in the two tubes 24 is measured separately and converted into a digital signal in an A/D converter 31.

Two signals I, II representing the pressures within the bladder 23a and the bladder 23b are coupled into a microcomputer 32. The microcomputer 32 is programmed so that oscillograms may be disregarded if the oscillogram is erroneous. If both oscillograms are valid, average values are formed. The systolic and diastolic blood pressure values and the pulse frequency are displayed on displays 33.

The pressure measurement, A/D conversion and the signal amplification may be performed by using several technology methods, e.g. pressure to frequency conversion, direct pressure to voltage conversion (Piezoelectric element) or any further known method.

Figure 8:
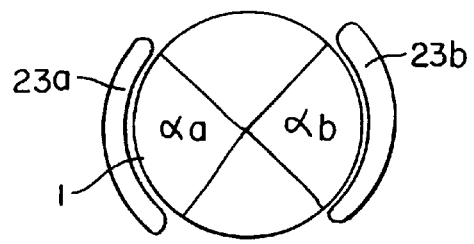
FIG. 8 is a schematic view of a cross-section through a human wrist.

FIG. 8 schematically shows a cross-section through a wrist indicating the angular extensions a,b of the two bladders 23a, 23b.

is about 90° in the specific use and may vary between about 40° and 150°

What is claimed is:

1. An apparatus for non-invasive measurement of the arterial blood pressure at the human wrist comprising
    a cuff having a shape adapted to be placed in a predetermined position around the wrist, and a blood pressure monitor for calculating and displaying blood pressure valves, said cuff having an ulnar measuring surface area adapted to be applied over the ulnar artery of the wrist and a radial measuring surface area adapted to be applied over the radial artery of the wrist,
    said cuff comprising a first bladder arranged in said ulnar measuring surface area and a second bladder arranged in said radial measuring surface area,
    each of said first and second measuring bladders having an angular extension and being disposed within the cuff in such a way that it lies within only one of said ulnar and radial measuring surface areas, and
    said first and said second measuring bladders being connected to said blood pressure monitor in such a way that the signals of said first and said second bladder may be treated separately in said blood pressure meter.

2. An apparatus according to claim 1, wherein the cuff comprises at least one marking for facilitating positioning of the cuff around the wrist.

3. An apparatus according to claim 1, wherein the apparatus is provided with a pneumatic double tube comprising a pair tubes, each tube being connected to each of said bladders.

4. An apparatus according to claim 1, further comprising, for each said bladder, a respective pneumatic pressure tube and a connector adapted to connect the tube to the blood pressure monitor.

5. An apparatus to claim 4, wherein the connector comprises a coding representing the location of the bladder within the cuff, the coding being detectable by the blood pressure monitor.

6. An apparatus according to claim 4, wherein the blood pressure monitor comprises a signal processing unit allowing simultaneous treatment of the signals provided by the two bladders.

7. An apparatus according to claim 1, wherein the bladder extends over and angle of 40°–150°.

8. A method for non-invasively measuring the arterial blood pressure at the human wrist said method comprising steps of:
    generating a first measuring signal with a first inflatable bladder arranged in a radial measuring surface covering the radial artery of the wrist,
    generating a second measuring signal with a second bladder arranged in an ulnar measuring surface covering the ulnar artery of the wrist,
    calculating the blood pressure on the basis of said first and said second signal in a calculating unit.

* * * * *